United States Patent
Robin

(10) Patent No.: US 7,713,228 B2
(45) Date of Patent: May 11, 2010

(54) SURGICAL METHOD

(75) Inventor: Alan L. Robin, Cockeysville, MD (US)

(73) Assignee: Alcon, Inc., Hunenberg (CH)

( * ) Notice: Subject to any disclaimer, the term of this patent is extended or adjusted under 35 U.S.C. 154(b) by 303 days.

(21) Appl. No.: 11/046,087

(22) Filed: Jan. 28, 2005

(65) Prior Publication Data

US 2006/0173437 A1 Aug. 3, 2006

(51) Int. Cl.
*A61N 1/30* (2006.01)

(52) U.S. Cl. .......................... 604/22; 604/521

(58) Field of Classification Search ................. 604/521, 604/22, 43, 500, 4
See application file for complete search history.

(56) References Cited

U.S. PATENT DOCUMENTS

| 3,930,505 A | * | 1/1976 | Wallach ...................... 604/22 |
| 4,607,622 A | | 8/1986 | Fritch et al. |
| 5,322,504 A | | 6/1994 | Doherty et al. |
| 5,360,399 A | * | 11/1994 | Stegmann ................... 604/521 |
| 5,478,338 A | | 12/1995 | Reynard |
| 5,562,692 A | * | 10/1996 | Bair .......................... 606/167 |
| 5,651,783 A | | 7/1997 | Reynard |
| 5,741,244 A | | 4/1998 | Klaas |
| 6,575,929 B2 | | 6/2003 | Sussman et al. |
| 6,726,676 B2 | * | 4/2004 | Stegmann et al. ........... 604/523 |
| 6,764,439 B2 | * | 7/2004 | Schaaf et al. ............... 600/106 |
| 2002/0013572 A1 | * | 1/2002 | Berlin .......................... 606/4 |
| 2002/0111608 A1 | * | 8/2002 | Baerveldt et al. .............. 606/6 |

* cited by examiner

*Primary Examiner*—Nicholas D Lucchesi
*Assistant Examiner*—Laura A Bouchelle
(74) *Attorney, Agent, or Firm*—Kenneth D. Bassinger

(57) ABSTRACT

An irrigating technique that can be used to increase the flow of fluid through the trabecular meshwork. Pulses of relatively high pressure irrigating are directed at the trabecular meshwork. These pulses can be focused, thereby perforating the trabecular meshwork, or applied over a larger area so as to stimulate the trabecular meshwork for improved fluid transport. In addition, the pulses of the irrigating balance salt solution can be used to clean away material, such as iris pigment, that may be blocking or clogging the trabecular meshwork. Such a technique may be practiced using the herein disclosed tip with commercially available surgical handpieces.

6 Claims, 2 Drawing Sheets

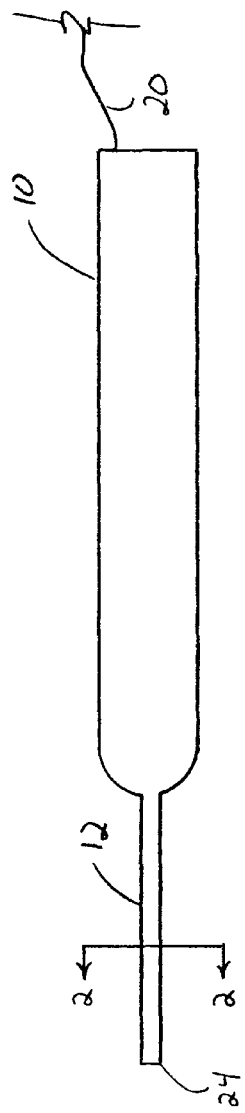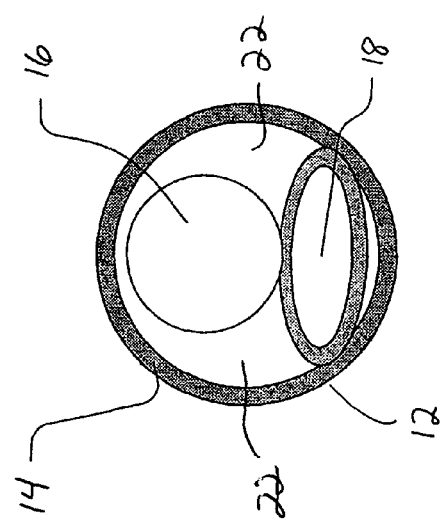

SURGICAL METHOD

BACKGROUND OF THE INVENTION

This invention relates generally to the field of eye surgery and more particularly to a method for glaucoma surgery.

Glaucoma affects approximately 2% of the population under 65 years of age and 11% over 65, and it is exceedingly difficult to diagnose and define. The eye is a hollow structure that contains a clear fluid called "aqueous humor." Aqueous humor is formed in the posterior chamber of the eye by the ciliary body at a rate of about 2.5 microliters per minute. The fluid, which is made at a fairly constant rate, then passes around the lens, through the pupillary opening in the iris and into the anterior chamber of the eye. Once in the anterior chamber, the fluid drains out of the eye through three different routes. Fluid can be absorbed by the iris, which normally accounts for less than 1% of drainage. In the "uveoscleral" route, fluid percolates between muscle fibers of the ciliary body. This route accounts for less than ten percent of the aqueous outflow in humans. The primary pathway for aqueous outflow in humans is through the "canalicular" route that involves the trabecular meshwork and Schlemm's canal.

The trabecular meshwork and Schlemm's canal are located at the junction between the cornea and the sclera. This is anterior to the insertion of the iris into the scleral. The junction or corner of the iris insertion and the cornea is called "the angle." The trabecular meshwork is a wedge-shaped structure that runs around the circumference of the eye. It is composed of collagen beams arranged in a three-dimensional sieve-like structure. The beams are lined with a monolayer of endothelial cells called trabecular cells. The spaces between the collagen beams are filled with an extracellular substance that is produced by the trabecular cells. These cells also produce enzymes that degrade the extracellular material. Schlemm's canal is adjacent to the trabecular meshwork. The outer wall of the trabecular meshwork coincides with the inner wall of Schlemm's canal. Schlemm's canal is a tube-like structure that runs around the circumference of the cornea. In human adults, Schlemm's Canal is believed to be divided by septa into a series of autonomous, dead-end canals.

The aqueous fluid travels through the spaces between the trabecular beams, across the inner wall of Schlemm's canal into the canal, through a series of collecting channels that drain from Schlemm's canal and into the episcleral venous system. In a normal situation, aqueous production is equal to aqueous outflow and intraocular pressure remains fairly constant with a mean of approximately 16 mm Hg. In glaucoma, the resistance through the canalicular outflow system is abnormally high, creating a higher intraocular pressure.

In primary open angle glaucoma, the most common form of glaucoma in the United States, the abnormal resistance is believed to be along the outer aspect of trabecular meshwork and the inner wall of Schlemm's canal. In normals, this accounts for approximately 50% of resistance. In glaucoma patients, this accounts for all of the additional resistance. It is believed that an abnormal metabolism of the trabecular cells might lead to an excessive build up of extracellular materials or a build up of abnormally "stiff" materials in this area. Histopathology of glaucoma eyes also demonstrates a collapse of Schlemm's canal. Primary open angle glaucoma accounts for approximately eighty-five percent of all glaucoma in the Americas and Europe. Other forms of glaucoma (such as angle closure glaucoma and secondary glaucomas) also involve decreased outflow through the canalicular pathway but the increased resistance is from other causes such as mechanical blockage, inflammatory debris, cellular blockage, etc.

With the increased resistance, the aqueous fluid builds up because it cannot exit fast enough. As the fluid accumulates, the intraocular pressure (IOP) within the eye increases. The increased IOP compresses the axons in the optic nerve and also may compromise the vascular supply to the optic nerve. The optic nerve carries vision from the eye to the brain. Some optic nerves seem more susceptible to a specific level of IOP than other eyes. While research is investigating ways to protect the nerve from an elevated pressure, the only therapeutic approach currently available in glaucoma that is proven either to prevent or retard the progression of nerve loss and resultant visual disability leading to blindness is to reduce the intraocular pressure.

The clinical treatment of glaucoma is commonly approached in a step-wise fashion. Medication often is the first treatment option. Usually administered either topically, these medications work to either reduce aqueous production or they act to increase outflow. Currently available medications have many serious systemic side effects including: congestive heart failure, respiratory distress, systemic hypotension, depression, sedation, renal stones, aplastic anemia, sexual dysfunction and death. As an asymptomatic disease, compliance with medical therapy is a major problem, with estimates that over half of glaucoma patients do not follow their correct dosing schedules. This lack of adherence to prescribed medical therapy may account for the fact that more than 20% of patients go blind bilaterally within a 20 year period.

When medication fails to adequately reduce the pressure, laser trabeculoplasty often is performed. In laser trabeculoplasty, energy from a laser is applied to a number of noncontiguous spots in the trabecular meshwork. It is believed that the laser energy stimulates the metabolism of the trabecular cells in some way, and changes the extracellular material in the trabecular meshwork. In approximately eighty percent of patients, aqueous outflow is enhanced and IOP decreases. However, the effect often is either not sufficient or not long lasting and at least fifty percent of patients develop an elevated IOP within five years. In many cases, the laser surgery is not usually repeatable. In addition, laser trabeculoplasty is not an effective treatment for primary open angle glaucoma in patients less than fifty years of age, nor is it effective for angle closure glaucoma and many secondary glaucomas.

If laser trabeculoplasty does not adequately reduce the IOP, then filtering surgery is performed. With filtering surgery, a hole is made in the sclera near the angle. This hole allows the aqueous fluid to leave the eye through an alternate route. The most commonly performed filtering procedure is a trabeculectomy. In a trabeculectomy, a conjunctiva incision is made, the conjunctiva being the transparent tissue that covers the sclera. The conjunctiva is moved aside, exposing the sclera at the limbus. A partial thickness scleral flap is made and dissected half-thickness into the cornea. The anterior chamber is entered beneath the scleral flap and a section of deep sclera and/or trabecular meshwork is excised. The scleral flap is loosely sewn back into place. The conjunctival incision is tightly closed. Post-operatively, the aqueous fluid passes through the hole, beneath the scleral flap which offers some resistance and collects in an elevated space beneath the conjunctiva called a bleb. The fluid then is either absorbed through blood vessels in the conjunctiva or traverses across the conjunctiva into the tear film.

Trabeculectomy and filtration surgery are both associated with many problems. Fibroblasts that are present in the episclera proliferate and migrate, and can scar down the scleral flap. Failure from scarring may occur, particularly in children, young adults, those with active inflammation or eyes with prior intraocular surgery. Of eyes that have an initially successful trabeculectomy, up to eighty percent will fail from scarring within three to five years after surgery. To minimize this scarring, surgeons now are applying antifibrotic agents such as mitomycin C (MMC) and 5-fluorouracil (5-FU) to the scleral flap at the time of surgery or giving injections of 5-FU daily for up to 14 days postoperatively. The use of these agents has increased the success rate of trabeculectomy but also has increased the prevalence of multiple complications which are sight-threatening and potentially blinding. The most serious complication is cataract which can occur in up to 20% of eyes. Bleb infections can occur in all eyes for the rest of the patient's life following surgery. Hypotony is a problem that develops when aqueous flows exits the eye faster than aqueous humor is made. The eye pressure drops too low (usually less than 6.0 mmHg); the structure of the eye collapses and vision decreases as the choroids and macula become swollen and folded.

Trabeculectomy also creates a pathway for aqueous fluid to escape to the surface of the eye. At the same time, it creates a pathway for bacteria that normally live on the surface of the eye and eyelids to get into the eye. If this happens, an internal eye infection can occur called endophthalmitis. Endophthalmitis often leads to permanent and profound visual loss. Endophthalmitis can occur anytime after trabeculectomy. The risk increases with the thin blebs that develop after MMC and 5-FU and is cumulative at about 0.4% per year. Another factor that contributes to infection is the placement of a bleb. Eyes that have trabeculectomy performed inferiorly have about eight times the risk of eye infection than eyes that have a superior bleb. Therefore, initial trabeculectomy is performed superiorly under the eyelid, in either the nasal or temporal quadrant.

In addition to scarring, hypotony and infection, there are other complications of trabeculectomy. The bleb can tear and lead to profound hypotony. The bleb can be irritating and can disrupt the normal tear film, leading to blurred vision. Approximately 67% of patients experience continuous persistent discomfort which can last for years. Patients with blebs generally cannot wear contact lenses. All of the complications from trabeculectomy stem from the fact that fluid is being diverted from inside the eye to the external surface of the eye.

Therefore, a need continues to exist for a surgical method for increasing the outflow of aqueous from the eye to help reduce IOP in glaucoma patients.

BRIEF SUMMARY OF THE INVENTION

The inventor of the present invention has discovered that the irrigating technique of the present invention can be used increase the flow of fluid through the trabecular meshwork. Pulses of relatively high pressure irrigating balanced salt solution can be directed at the trabecular meshwork. These pulses can be focused, thereby perforating the trabecular meshwork, or applied over a larger area so as to stimulate the trabecular meshwork for improved fluid transport. In addition, the pulses of the irrigating fluid can be used to clean away material, such as iris pigment, that may be blocking or clogging the trabecular meshwork. Such a technique may be practiced using the herein disclosed tip with commercially available surgical handpieces.

Accordingly, one objective of the present invention is to provide a surgical method for treating glaucoma.

Another objective of the present invention is to provide a surgical method for increasing the outflow out of the eye through the trabecular meshwork.

These and other advantages and objectives of the present invention will become apparent from the detailed description and claims that follow.

BRIEF DESCRIPTION OF THE DRAWINGS

FIG. 1 is an elevational view of a handpiece that may be used with the method of the present invention.

FIG. 2 is an enlarged cross-sectional view of the tip of the handpiece illustrated in FIG. 1 taken at line 2-2 in FIG. 1.

DETAILED DESCRIPTION OF THE INVENTION

Figure 3:
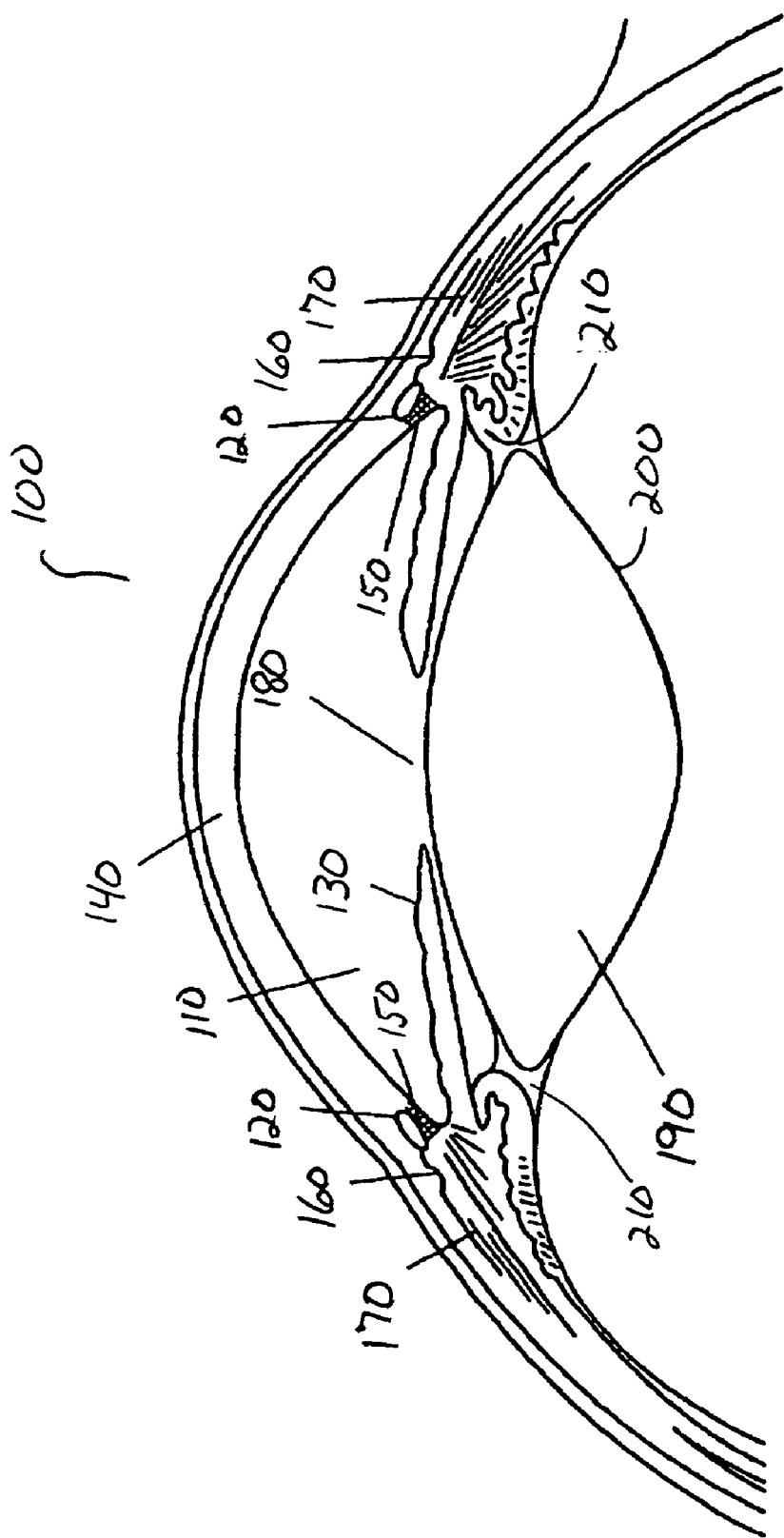
FIG. 3 is an illustration showing the anatomic details of the human eye.

As best seen in FIG. 1, the method of the present invention may be practiced using handpiece 10 having tip 12. Handpiece 10 may be any suitable handpiece capable of delivering pulses of irrigating fluid (e.g., balanced salt solution) through tip 12. Examples of suitable handpieces 12 are disclosed in U.S. Pat. No. 6,575,929 (Sussman, et al.), U.S. Pat. No. 5,322,504 (Doherty, et al.) and U.S. Pat. No. 5,562,692 (Bair) and commercially available from sources such as Alcon Laboratories, Inc., Fort Worth, Tex. and sold under the trademark AQUALASE®.

Tip 12 contains outer tube 14 which may be made from a fiber optic material or contain optical fibers so as to provide a source of illumination for the surgical field. Alternatively, tube 14 may be opaque and a second illumination probe (not shown) or no illumination probe may be used. Tip 12 may contain fiber optic 16 which provides a light path for a camera or other visualization device (not show) so that the surgical site can be visualized more easily by the surgeon through cable 20. Tip 12 also contains fluid channel or tube 18 through which the pulses of irrigating fluid are projected at the interior portion of eye 100. Interior portion 22 of tube 14 not occupied by tube 18 and fiber optic 16 may be used for other functions, such as aspiration. Outer tube 14, fiber optic 16 and tube 18 are made from conventional materials using conventional construction methods well-known in the art.

The surgical anatomy relevant to the present invention is illustrated in FIG. 3. Generally, FIG. 3 shows eye 100 having anterior chamber 110, Schlemm's canal 120, iris 130, cornea 140, trabecular meshwork 150, collecting channels 160, episcleral veins 170, pupil 180, lens 190, posterior capsule 200 and capsule equatorial region 210.

In use, distal end 24 of tip 12 is placed in or near trabecular meshwork 150 in anterior chamber 110 of eye 100 using, for example, an incision in cornea 140 and a surgical technique similar to that used in phacoemulsification surgery. Pulses of fluid will be directed out of tube 18 and toward trabecular meshwork 150. The fluid pulses can be focused, thereby perforating trabecular meshwork 150, or applied over a larger area so as to stimulate trabecular meshwork 150 for improved fluid transport. In addition, the pulses of the irrigating fluid can clean or clear away material, such as iris pigment, that may be blocking or clogging trabecular meshwork 150.

This description is given for purposes of illustration and explanation. It will be apparent to those skilled in the relevant art that changes and modifications may be made to the invention described above without departing from its scope or spirit. For example, it will be recognized by those skilled in the art that the present invention may be combined with ultrasonic and/or rotating or boring cutting tips to enhance performance.

I claim:

1. A method for treating glaucoma, comprising the steps of:
   a) inserting a handpiece tip having a distal end into an eye's anterior chamber through an incision in the cornea;
   b) placing the distal end at or near a trabecular meshwork of the eye; and
   c) causing repeated focused pulses of an irrigating fluid to strike the trabecular meshwork, wherein the focused pulses perforate the trabecular meshwork.

2. The method of claim 1 wherein the pulses stimulate the trabecular meshwork.

3. The method of claim 1 wherein the pulses clear away iris pigment blocking or clogging the trabecular meshwork.

4. The method of claim 1 wherein the pulses are applied over a relatively large portion of the trabecular meshwork.

5. A method for treating glaucoma, comprising the steps of:
   a) inserting a handpiece tip having a distal end into an eye's anterior chamber through an incision in the cornea;
   b) placing the distal end at or near a trabecular meshwork of the eye; and
   c) causing repeated pulses of an irrigating fluid to strike the trabecular meshwork, wherein the pulses stimulate the trabecular meshwork and clear away material clogging the trabecular meshwork.

6. The method of claim 5 wherein the pulses are applied over a relatively large portion of the trabecular meshwork.

* * * * *